(12) United States Patent
Benchetrit

(10) Patent No.: US 7,824,422 B2
(45) Date of Patent: Nov. 2, 2010

(54) ADJUSTABLE GASTROPLASTRY RING COMPRISING A GRIP TAB

(75) Inventor: Salomon Benchetrit, Caluire (FR)

(73) Assignee: Compagnie Européenne d'etude et de Recherche de Dispositifs pour l'Implatation Par Laporoscopie, Vienne (FR)

( * ) Notice: Subject to any disclaimer, the term of this patent is extended or adjusted under 35 U.S.C. 154(b) by 457 days.

(21) Appl. No.: 10/275,019

(22) PCT Filed: May 11, 2001

(86) PCT No.: PCT/FR01/01434

§ 371 (c)(1),
(2), (4) Date: Jun. 26, 2003

(87) PCT Pub. No.: WO01/85071

PCT Pub. Date: Nov. 15, 2001

(65) Prior Publication Data

US 2004/0049209 A1    Mar. 11, 2004

(30) Foreign Application Priority Data

May 12, 2000    (FR)    ................... 00 06329

(51) Int. Cl.
*A61B 17/08*    (2006.01)
*A61F 2/04*    (2006.01)
*A61F 13/00*    (2006.01)

(52) U.S. Cl. ........................ 606/157; 606/151; 606/153; 606/201; 606/202; 606/203; 623/23.65; 600/29; 600/30; 600/31; 600/32; 600/37; 604/909

(58) Field of Classification Search .................. 606/151, 606/153, 157, 201–203; 623/23.65; 600/29–32, 600/37; 604/909
See application file for complete search history.

(56) References Cited

U.S. PATENT DOCUMENTS

| 2,660,174 A | * | 11/1953 | Saemann | ...................... 606/202 |
| 4,592,339 A | * | 6/1986 | Kuzmak et al. | ............. 128/899 |
| 4,803,985 A | * | 2/1989 | Hill | .............................. 606/157 |
| 5,074,868 A |   | 12/1991 | Kuzmak | ..................... 606/157 |
| 5,152,770 A | * | 10/1992 | Bengmark et al. | .......... 606/157 |

(Continued)

FOREIGN PATENT DOCUMENTS

DE    G 90 14 048.6    12/1990

(Continued)

*Primary Examiner*—Thomas C Barrett
*Assistant Examiner*—Sameh Boles
(74) *Attorney, Agent, or Firm*—Thomas, Kayden, Horstemeyer & Risley, LLP

(57) ABSTRACT

The invention relates to a gastroplasty ring formed by a flexible band (2) which comprises a first end part (5) and a second end part (6) and which is intended to be closed around the stomach toward its two end parts by a closure system in order to reduce the diameter of the opening of the stoma by forming a loop, the band comprising an adjustable-volume annular compression chamber (3) connected, at the first end part, by an adjusting catheter (7) to a device for adjusting the internal pressure of said chamber, so as to adjust its diametral expansion, the ring comprising at least one grab tab (11, 12, 13) which projects toward the outside of the loop to make it easier for the two end parts to be brought together and parted.

Gastric implant for treating obesity.

20 Claims, 1 Drawing Sheet

U.S. PATENT DOCUMENTS

| | | | | |
|---|---|---|---|---|
| 5,160,338 | A | * | 11/1992 | Vincent ...................... 606/157 |
| 5,226,429 | A | * | 7/1993 | Kuzmak ..................... 128/898 |
| 5,449,368 | A | * | 9/1995 | Kuzmak ..................... 606/157 |
| 5,601,604 | A | * | 2/1997 | Vincent ...................... 606/216 |
| RE36,176 | E | * | 3/1999 | Kuzmak ..................... 606/157 |
| 5,919,233 | A | * | 7/1999 | Knopf et al. ................ 128/898 |
| 5,938,669 | A | * | 8/1999 | Klaiber et al. .............. 606/157 |
| 6,102,922 | A | * | 8/2000 | Jakobsson et al. ........... 606/157 |
| 6,676,674 | B1 | * | 1/2004 | Dudai ........................ 606/151 |
| 6,966,875 | B1 | * | 11/2005 | Longobardi .................. 600/31 |
| 7,172,607 | B2 | * | 2/2007 | Hoefle et al. ................ 606/151 |

FOREIGN PATENT DOCUMENTS

DE      G 197 51 733      12/1998

* cited by examiner

ADJUSTABLE GASTROPLASTY RING COMPRISING A GRIP TAB

CROSS REFERENCE RELATED APPLICATIONS

This application is a national phase of PCT/FR01/01434 filed May 11, 2001, which claims priority to French Application Serial No. 00/06329 filed May 12, 2000.

TECHNICAL FIELD

The present invention relates to the technical field of surgical implants intended to treat obesity by implanting a flexible gastric band intended to restrict the stomach of a patient, said gastric band being equipped with an annular compression chamber, the volume of which is variable and can be adjusted via an adjusting catheter connected to an adjusting and control device implanted in the body of the patient.

The present invention relates to a gastroplasty ring formed by a flexible band which comprises a first end part and a second end part and which is intended to be closed around the stomach essentially toward and by its two ends, using a closure system so as to reduce the diameter of the opening of the stoma by forming a loop, the band comprising an adjustable-volume annular compression chamber connected, at one of the end parts, by an adjusting catheter to a device for adjusting the internal pressure of said chamber, so as to adjust its diametral expansion.

PRIOR ART

In the case of patients suffering from extremely severe obesity (morbid obesity), that is to say in the case of patients whose weight exceeds the ideal weight by at least fifty kilos, for example, it is absolutely essential to treat these patients surgically in order not only to avoid a series of health problems ensuing from this obesity, but also to avoid certain and precipitate death of such patients.

Indeed, it is acknowledged that patients suffering from morbid obesity present a significantly reduced life expectancy, the reduction being by at least some ten to fifteen years, while at the same time creating significant problems of physchological burden. Furthermore, a whole series of ancillary health phenomena are involved, having an impact on the development of cardiovascular diseases, hypertension, diabetes, and severe arthritis in particular.

It has been found that treatment based on a strict diet combined with a series of physical exercises associated with a modification in behavior, particularly eating habits, were not very well suited to such cases of morbid obesity, even though such treatment methods are the most healthy.

This is why treatments for morbid obesity which are effective and remain so in the long-term, involve surgical treatment.

In general, a distinction is made between surgical treatment techniques involving a lack of absorption of foodstuffs, that is to say a shortening of the conventional path of the food and of the digestive juices, and techniques involving gastric restriction, reducing the size of the stomach.

Surgical techniques involving a lack of absorption are, for example, those involving a technique of bypassing the small intestine or alternatively those separating the passage of the foodstuffs relative to the digestive juices. The surgical technique of bypassing may give rise to severe complications, which means that this technique is now used only very rarely. The surgical technique of separating the passage of the alimentary bolus relative to the digestive juices does not involve particular complications, but entails a major surgical operation involving, in particular, a partial gastrectomy.

This is why the trend nowadays is to use surgical techniques employing gastric restriction to reduce the intake of food.

Such techniques conventionally involve the use of gastroplasty rings implanted around the stomach in order to reduce its size and the diameter of its passage (stoma).

Most of the known gastroplasty devices, and, for example, the one described in U.S. Pat. No. 5,074,868, employ a flexible band made of an elastomeric material and intended to be implanted around the stomach then tightened and closed into a loop of fixed diameter by a closure system. The body of the flexible band contains a variable-volume compression chamber or cavity connected by an adjusting catheter to a device for adjusting the internal pressure of the chamber so as to vary the inside diameter of the loop in order to modify or adjust the diameter of the stoma by injecting or extracting a volume of liquid into or from the chamber. Such an operation of adjusting the inside diameter of the ring is performed using conventional control devices including a miniaturized unit implanted directly under the skin of the patient and equipped with a self-sealing membrane through which the doctor injects or withdraws liquid using a syringe.

The closure system of U.S. Pat. No. 5,074,868 employs suturing, using sutures, of the two parts of the flexible band of the ring.

Such a device is generally satisfactory but, like most of the known systems, suffers from disadvantages associated essentially with the difficulty involved in any surgical operation likely to arise once the gastroplasty implant has been fitted. What has been found is that in spite of the possibility of, to a certain extent, altering the diameter of the ring without surgical intervention, using the miniaturized unit mentioned hereinabove, the fitting of such gastric implants may be accompanied by phenomena of intolerance, for example accompanied by vomiting, associated with an excessive reduction in the diameter of the stoma, or alternatively with ineffective action of the implant associated with an excessively large diameter of the stoma, or alternatively still, quite simply with discomfort or a local or generalized infection or inflammation.

This is why it is often necessary to perform a further surgical operation, either to make the patient more comfortable, or to modify or change the gastroplasty ring already implanted. Such surgical operations are particularly severe and in addition entail either a surgeon cutting the ring, or the cutting of the suture accompanied by a complete opening of the ring followed by its exchange and replacement.

Such operations are tricky to perform, are difficult for the patient to tolerate, and are therefore expensive in that they entail destroying an implant and replacing it.

SUMMARY OF THE INVENTION

The object of the invention is therefore to propose a novel gastroplasty ring making it possible to remedy the various drawbacks listed above and which is capable of making the ring easier to handle when the implant is being fitted and when the ring is being opened and closed again during a further operation.

Another object of the invention is to propose a novel gastroplasty ring capable simply and reliably of reversibly closing the loop that makes up the ring while at the same time allowing easy unlocking of the end parts, doing so without entailing destruction of the implant.

Another object of the invention is to propose a novel gastroplasty ring capable of offering a simple and reliable means of adapting the diameter of the ring to suit each given surgical situation.

Another object of the invention is to propose a novel gastroplasty ring capable of exhibiting several implantation diameters.

Another object of the invention is to propose a novel gastroplasty ring making it possible to reduce the discomfort experienced by the patient, while at the same time being firmly held in place by the loop.

Another object of the invention is to propose a novel gastroplasty ring which is particularly easy to manufacture while at the same time having excellent overall mechanical strength.

The objects of the invention are achieved using a gastroplasty ring formed by a flexible band which comprises a first end part and a second end part and which is intended to be closed around the stomach toward its two end parts by a closure system in order to reduce the diameter of the opening of the stoma by forming a loop, the band comprising an adjustable-volume annular compression chamber connected, at the first end part, by an adjusting catheter to a device for adjusting the internal pressure of said chamber, so as to adjust its diametral expansion, characterized in that the ring comprises grab tabs which project toward the outside of the loop to make it easier for the two end parts to be brought together and parted.

BRIEF DESCRIPTION OF THE DRAWINGS

Further objects and advantages of the invention will become better apparent from reading the appended description, and with the aid of the purely illustrative and informative appended drawings, in which.

BEST EMBODIMENT OF THE INVENTION

Figure 1:
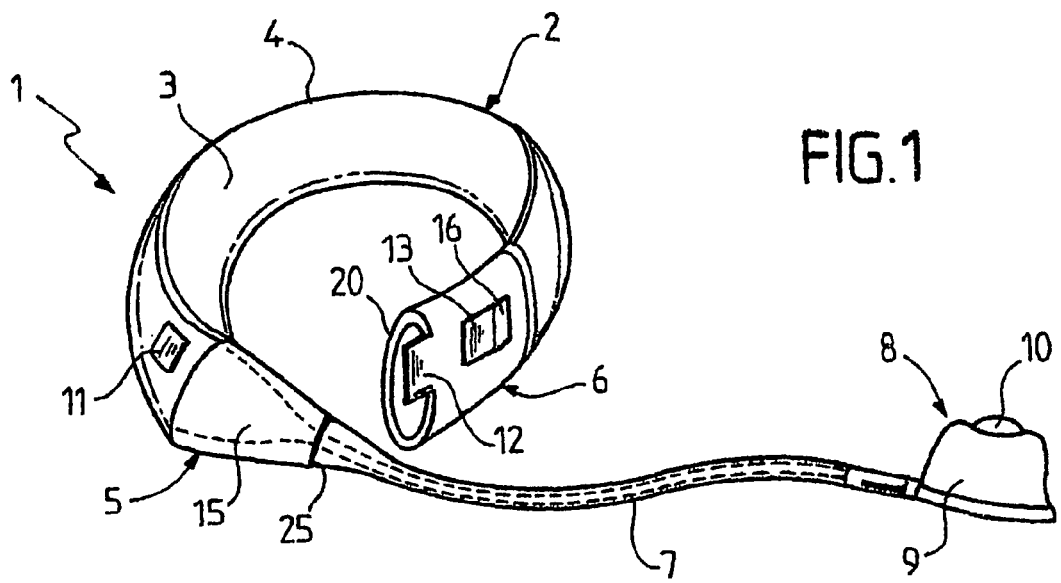
FIG. 1 illustrates, in a schematic perspective view, one embodiment of a gastroplasty ring according to the invention, in the open position prior to its being implanted.
Figure 2:
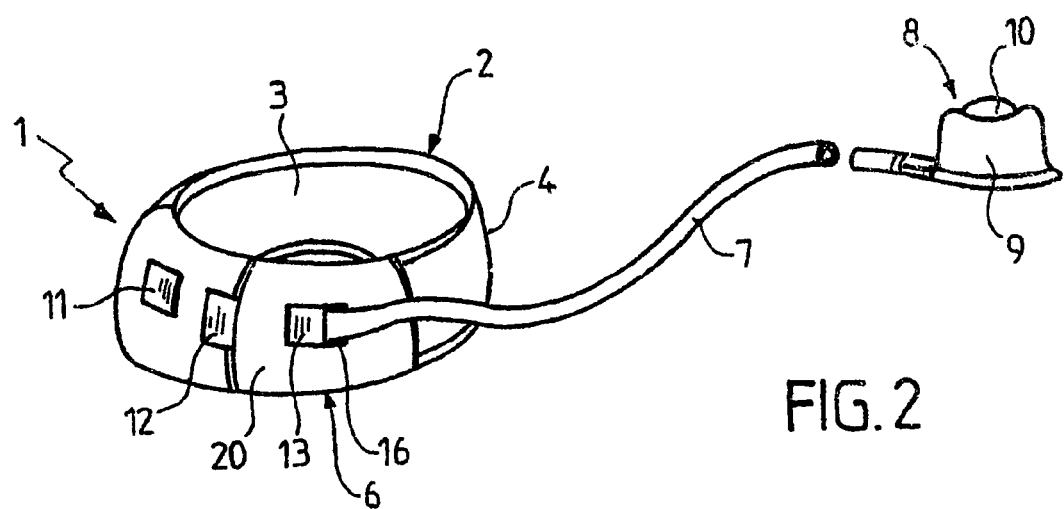
FIG. 2 illustrates, in a schematic perspective view, one embodiment of a gastroplasty ring according to the invention, in the closed position.
Figure 3:
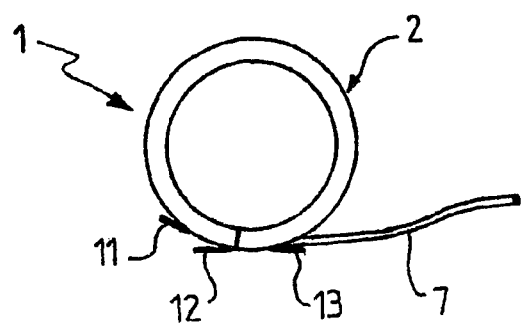
FIG. 3 illustrates, in a view from above, the gastroplasty ring in FIG. 2.

FIGS. 1 and 2 illustrate a preferred embodiment of a gastroplasty ring 1 according to the invention, formed by a flexible band 2 produced, for example, by thermoforming, from an elastomeric material for surgical use, said band 2 defining, preferably essentially along its entire length, an internal compression chamber 3 delimited by the walls 4 of the flexible band 2 and by a first end part 5 and a second end part 6.

In its position of implantation in the stomach of a patient, as illustrated in FIG. 2, the compression chamber 3 therefore forms an annular compression chamber.

As is well known in the prior art, the compression chamber 3 defines a closed volume internal to the gastroplasty ring, which is intended to form a volume which is adjustable so that the diametral expansion of the ring can be adjusted when the ring is in place so as to adapt it to suit each given surgical situation.

In the conventional way, the diametral expansion of the gastroplasty ring according to the invention is adjusted by an adjusting catheter 7 formed by a tubular element made of elastomeric material extending one of the free end parts, for example the first end part 5, of the compression chamber 3 so as to connect said chamber to a device 8 for adjusting the internal pressure of said chamber.

As is well known to those skilled in the art, the adjusting device 8 may be formed by a miniaturized unit 9 implanted under the skin of the patient. The miniaturized unit 9 comprises, for example, a self-sealing upper membrane 10 intended to be pierced by a syringe so that a certain amount of fluid can be injected or withdrawn so as to vary the volume of the compression chamber 3, in order to adjust the volume of the chamber and thus obtain the desired inside diameter of the ring. As a device such as this is well known to those skilled in the art, it will therefore not be described further in detail.

The gastroplasty ring according to the invention also comprises a closure system intended to close the gastroplasty ring in a loop around the stomach and hold it in position.

According to an important feature of the invention, the ring further comprises at least one grab tab which projects outward from the loop to make it easier for the two end parts to be brought together and parted when the ring is being closed and/or during a further operation in order to adjust the ring, when unlocking it or alternatively when relocking it.

As depicted in the figures, the flexible band 2 has, near the first end part 5 of the ring, at least one first grab tab 11.

As a preference, the second end part 6 comprises a second grab tab 12 and, advantageously, it also bears a third grab tab 13.

Each of the grab tabs 11, 12, 13, is preferably essentially flat and extends between a first end which is secured to the walls of the ring and a second end which is free and can be grasped by gripping so as to positively move at least one of the end parts 5 and 6.

Also as a preference, the grab tabs are flexible so that they can move out of the way when the ring is being introduced into the body of the patient. They are of rectangular shape.

Each of the grab tabs extends tangentially to the walls 4 of the ring 1 so that it is perpendicular to the plane of this ring and is of a small size with respect to the overall dimensions of the ring. In particular, the thickness of the tabs is slender with respect to their width and to their length.

The grab tabs are formed integrally with the band and the walls of the end parts 5 and 6 or are attached and secured to these by any mechanical or chemical means, such as by bonding or overmolding, for example, while being made of a biocompatible elastomeric material.

In general, the grab tabs form protrusions which can be implanted at any point on the external surface or internal surface of the walls of the band and of the end parts, so as to be grabbed by the surgeon using any surgical instrument such as forceps, for example, so as to make the ring easier to handle, to lock and to unlock.

Also as a preference, the first grab tab 11 extends in the opposite direction to the second end part 6. The second grab tab 12 extends in the same direction as the first tab 11, while the third tab 13 is in the opposite direction to the other two tabs 11 and 12.

According to one feature of the invention, the closure system according to the invention comprises means for immobilizing and slackening the ring, which means are carried by the adjusting catheter 7, thus making it possible, starting from the position in which the ring is diametrically immobilized, corresponding to the closed and loop-shaped position as illustrated in FIG. 2, for it to be diametrically released for a moment by a relative movement of the two end parts 6, 7 of the ring, while at the same time, if so desired, forming a closed loop around the stomach. Advantageously, the immobilizing and slackening means are reversible.

According to the invention, the immobilizing and slackening means comprise pneumatic means for closing and opening the ring, involving a fluid, for example a gas or a liquid. Recourse to pneumatic means allows simplified placement of the implant and simple control over its opening and closure.

Performing such a technical function makes it possible, in addition to the simplicity of placement and of closure of the ring that it affords, to reduce the severity and impact of any repeat surgical interventions following the placement of an implant by avoiding having to cut through and to destroy the gastroplasty ring fitted. A function such as this allows the ring to be opened up easily using the first and third grab tabs 11, 13 and even the second tab, without destroying the loop of the ring, possibly allows the ring to be left in place, and allows subsequent re-locking using the second tab 12.

According to a preferred alternative form of the invention, as illustrated in FIGS. 1 and 2, the gastroplasty ring according to the invention comprises a closure system, the reversible immobilizing and slackening means of which comprise at least one deformable zone 15 and an opening 16 formed in the wall 4 of the second end part 6 of the band 2. The inflatable adjusting catheter 7 which is made of a biocompatible elastomeric material, is intended to be slipped into the opening 16, when the ring is in the closed position, and also to act as a guide means.

The deformable zone 15 may form a protrusion if the pressure in the adjusting catheter 7 increases, said protrusion resting against the walls 4 of the end part 6 of the band, inside the chamber 3, so as to immobilize the ring in the closed position. The protrusion reverts to its shape at rest if the pressure inside the adjusting catheter 7 returns to normal, so as to allow said catheter to slide and be guided freely in the opening 16, and so as to allow the loop to be slackened.

According to one particularly advantageous version of the invention, the reversible deformable zone 15 is formed by at least one zone of lesser strength and, in its shape at rest, constitutes a zone of a shape that converges toward the second end part 6. It may, for example, be of triangular shape in cross section, that is to say in a plane of section perpendicular to the plane of the ring.

Advantageously, the deformable zone 15 may be formed by a section of the adjusting catheter 7 having a hardness of the elastomeric material of which the catheter is made, which is locally lower than the overall hardness of said catheter. In such a case, as the adjusting catheter 7 is connected to the external adjusting device 8 for pressurizing using a fluid (air or liquid), the zone 15 will tend to form a kind of balloon with a diameter greater than the internal dimensions of the band, which will diametrically immobilize the ring. The pressurizing of the balloon occurs before the band is pressurized, this being facilitated by the convergent shape of the balloon.

Advantageously, the flexible band 2 is provided at one end part, and for example at the second end part 6 opposite the first end part 5 which is extended via the adjusting catheter 7, with a hollow sleeve 20 extending the flexible band 2.

The hollow sleeve 20 also comprises the opening 16 which is formed in one of its faces, preferably an external face, so that the other end 5 of the flexible band 2 can be inserted in said sleeve in the closed position, the adjusting catheter 7 then passing through the opening 16 (FIG. 2) to form the loop of the ring. Such a constructional arrangement makes the withstand of the closure very reliable while at the same time allowing the compression chamber 2 to extend around the entire perimeter for clamping the stomach.

As a preference, the band 2 and the hollow sleeve 20 are of a cross section of oblong shape to make it even easier still for the deformable zone 15 to become jammed when it is pressurized.

Advantageously, the flexible band 2, the compression chamber 3 and the hollow sleeve 20 form a one-piece unit made from one and the same elastomeric plastic, the adjusting catheter 7 then being hot-welded on.

As a preference, the third grab tab 13 extends from the external surface of the sleeve, and partly over the opening 16 without, however, impeding the passage of the catheter through this opening.

Advantageously, it is also possible for the deformable zone 15 to be made with a thickness which differs from the thickness of the flexible band 2 so as to obtain different fluid flow rates through each of these elements. These different flow rates may also be obtained by different shapes, the purpose of this being, for example, to deflate the flexible band 2 before the deformable zone 15.

The end part 5 of the band 2 to which the adjusting catheter 7 is connected is preferably of conical shape to make it easier to insert into the hollow sleeve 20. The deformable zone 15 is situated inside this conical shape.

Also as a preference, the adjusting catheter 7 has a limit stop 25 which is situated at the end of the conical part, near the deformable zone 15, and which is intended to pass through the opening 16 of the hollow sleeve 20. After this limit stop has clipped into the opening 16, the protrusion 15 may be immobilized by inflation.

These limit-stop means 25 consist for example of an excess of material forming a lump facing toward the outside of the ring and which prevents unwanted unfastening of the ring. The clipping of these means also makes it possible to check that the catheter has been slipped far enough into the opening 16 for the nominal ring diameter to be achieved, and also make sure that the protrusion is held in position immobilized in the hollow sleeve 20.

Furthermore, the adjusting catheter 7 is essentially rigid and is of great length by comparison with the diameter of the ring, so as to facilitate the operation of slipping and passing the catheter 7 into and through the opening 16. This also allows good placement of the band in the desired position.

Producing a gastroplasty ring in one piece makes it possible to simplify the method of manufacture of the ring and to obtain a ring which presents no risk of degradation over time.

During implantation, the ring according to the invention is set in place around the stomach in the position illustrated in FIG. 1. As the adjusting device 8 is disconnected to start with, the surgeon slips the adjusting catheter 7 into the opening 16 and passes it through the latter so as to insert the first end part 5 into the hollow sleeve 20 (FIG. 1). The surgeon then brings the limit stop 25 into the immobilizing position in the opening 16 using the second grab tab 12. He may then, using the adjusting and inflation device 8 connected to the single catheter 7, immobilize the ring in position. The surgeon then adjusts the internal diameter of the ring by injecting or removing the appropriate amount of liquid through the catheter 7. It will be noted that all of these operations are carried out using one single solitary catheter 7.

In the event of a further surgical operation, it is possible, by virtue of the gastroplasty ring according to the invention, for the operation to be confined to a superficial external examination of the situation of the implant using celioscopy or laparoscopy, simply by optical inspection using a camera. As appropriate, if the situation so demands, it is possible in a first instance, to unlock the catheter using simple celioscopy. To do this, all that is required is for the catheter 7 to be put under depression, which leads to deflation of the band and to a release of the balloon. All that is then required is for the two end parts 5 and 6 to be detached by action on the first and third locking tabs 11, 13. The tabs therefore allow the limit stop 25 to be disengaged from the opening 16. The catheter may then be slid through the opening 16. It is also possible to use the second grab tab 12 to extract the limit stop and to open out the ring; the ring is then turned back on itself in the opposite direction to the first grab tab 11.

Such sliding is accompanied by a partial and momentary slackening of the ring, without having to perform a serious operation on the patient.

It may be pointed out that the gastroplasty ring according to the invention has grab tabs which, during unlocking, are manipulated in opposite directions so that the ring experiences essentially symmetric opposed forces. During unlocking, the ring therefore does not have a tendency to move the part of the stomach around which it is placed.

It is then possible, also by a simple laparoscopic examination and operation, to close the ring again and immobilize it in the closed position in a very simple way, because the loop of the ring has never been destroyed.

It will therefore be understood that the grab tabs 11 to 13 have the function of facilitating the locking of the ring and of making it possible to unlock the ring without destroying this ring.

INDUSTRIAL APPLICABILITY

The invention finds its industrial application in the production and use of gastroplasty rings.

The invention claimed is:

1. A gastroplasty ring configured to form a loop about a stomach having a stoma, comprising:
   a flexible band having an outside surface and a first end part and a second end part;
   a closure system for reducing a diameter of an opening of the stoma by forming a loop around the stomach towards the first and the second end parts; and
   at least one grab tab projecting from said outside surface of the loop, the at least one grab tab being configured to assist in joining and separating the two end parts, the at least one grab tab comprising:
   a first grab tab, disposed proximal to the first end part, configured for separating the first end part from the second end part; and
   a second grab tab, spaced from the first and disposed at the second end part, configured for joining the first end part and the second end part together and further configured to unlock the first end part from the second part;
   said grab tabs being configured to be simultaneously manipulated in opposite directions during unlocking such that said ring experiences essentially symmetric opposed forces for providing partial and momentary slacking of the ring.

2. The ring as claimed in claim 1, wherein the at least one grab tab further includes a third grab tab disposed on the second end part, thereby allowing the second end part to be parted from the first end part.

3. The ring as claimed in claim 2, wherein the grab tabs are of essentially flat shape and extend between a first end which is secured to the ring and a second end which is free and can be grasped by gripping so as to positively move the ring end part on which the grab tab is mounted.

4. The ring as claimed in claim 3, wherein the first grab tab faces in the opposite direction to the second end part, the second grab tab faces in the same direction as the first grab tab, and the third grab tab faces away from the second grab tab.

5. The ring as claimed in claim 1, wherein the closure system further comprises pneumatic means for closing and opening the ring.

6. The ring of claim 1, further comprising:
   an adjustable-volume annular compression chamber being connected at the first end part to an adjusting catheter, the adjusting catheter configured for connection to a device for adjusting the internal pressure of the chamber to adjust the diametrical expansion of the chamber.

7. The ring as claimed in claim 6, wherein the closure system further comprises pneumatic means for closing and opening the ring and the pneumatic means are carried by the adjusting catheter and include at least one deformable zone, an opening is formed in the wall of the second end part of the band, the adjusting catheter sliding in the opening to form the loop of the ring, the deformable zone being configured to form a protrusion in the event of an increase in the pressure in the catheter, said protrusion resting against the interior walls of the band so as to immobilize the ring in a closed position and, the deformable zone being capable of reverting to an original shape in the event of a return to normal pressure, so as to allow the adjusting catheter to slide freely and the loop to be slackened.

8. The ring as claimed in claim 7, wherein the deformable zone is a zone of lesser strength formed on the adjusting catheter.

9. The ring as claimed in claim 7, wherein the second end part of the flexible band includes a hollow sleeve, said sleeve having the opening so that the first end part of the band can be inserted in the sleeve.

10. The ring as claimed in claim 9, wherein the first end part of the flexible band is of convergent shape and includes the deformable zone which is of triangular shape in cross section.

11. The ring as claimed in claim 10, wherein the cross section of the band is of oblong shape.

12. The ring as claimed in claim 6, wherein the device for adjusting the internal pressure of the chamber is a compression/decompression device.

13. The ring as claimed in claim 1, wherein the second end part of the flexible band includes a hollow sleeve, said sleeve having an opening for the first end part of the band can be inserted in to the hollow sleeve.

14. A gastroplasty device comprising:
   a flexible band having an outside surface and a first end and a second end, the band configured to form a loop about a stomach by the first and second ends at a time when the band is in a closed position;
   a system configured to releasably lock the first and second end in the closed position and to unlock the first and second ends; and
   grabbing means, projecting outwardly from said outside surface of the band, for manipulation by substantially opposing symmetric forces to move the first and second ends into, and out of, the closed position;
   wherein the grabbing means comprises a first tab located proximate the first end and a second tab located proximate the second end, the first and second tabs configured to be manipulated in opposite directions in order to move the first and second ends into the closed position.

15. The device of claim 14, wherein the grabbing means further comprises a third tab proximate the second end and positioned between the first tab and the second tab at a time when the band is in an open position.

16. The device of claim 15, wherein the first tab and the second tab are configured to be simultaneously manipulated by opposing forces to move the first and second ends into the closed position, and the first tab and the third tab are configured to be simultaneously manipulated by opposing forces in order to move the first and second ends out of the closed position.

17. The device of claim 14, wherein the second end includes an opening in the surface and the first end includes a deformable portion configured for insertion into and through the opening at a time when the band is in the closed position.

18. The device of claim 17, wherein the grabbing means comprises a first tab extending from the surface that is proximate the first end and a second tab extending from the surface that is proximate the second end and, at a time when the band is in an open position, the opening is located on the surface at a position between the first tab and the second tab.

19. The device of claim 18, wherein the grabbing means further comprises a third tab extending from the surface and adjacent to the opening and, at a time when the band is in the open position, the third tab is located on the surface between the first tab and the second tab.

20. The device of claim 17, wherein the grabbing means comprises a first tab proximate the first end, a second tab proximate the second end, and a third tab adjacent to the opening and:

- at a time when the band is in the closed position, the opening is positioned on the outside of the ring in a portion of the surface between the first tab and the second tab, and the second tab is positioned between the first tab and the third tab; and
- at a time a time when the band is in an open position, the opening and the third tab are positioned on the outside of the ring on a portion of the surface between the first tab and the second tab.

* * * * *